United States Patent
Sluis

(10) Patent No.: US 6,506,155 B2
(45) Date of Patent: Jan. 14, 2003

(54) DATA ENTRY AND SETUP SYSTEM AND METHOD FOR ULTRASOUND IMAGING

(75) Inventor: Doug Sluis, Mukilteo, WA (US)

(73) Assignee: ATL Ultrasound, Inc., Bothell, WA (US)

( * ) Notice: Subject to any disclaimer, the term of this patent is extended or adjusted under 35 U.S.C. 154(b) by 0 days.

(21) Appl. No.: 09/737,713

(22) Filed: Dec. 15, 2000

(65) Prior Publication Data

US 2002/0077547 A1 Jun. 20, 2002

(51) Int. Cl.[7] ................................................ A61B 8/00
(52) U.S. Cl. ....................................................... 600/437
(58) Field of Search ................................ 600/437, 443, 600/447; 382/128; 705/2

(56) References Cited

U.S. PATENT DOCUMENTS

| | | | | |
|---|---|---|---|---|
| 5,291,399 A | * | 3/1994 | Chaco ................... | 364/413.02 |
| 5,603,323 A | | 2/1997 | Pflugrath et al. ...... | 128/660.01 |
| 5,897,498 A | | 4/1999 | Canfield, II et al. ........ | 600/437 |
| 5,997,478 A | | 12/1999 | Jackson et al. ............. | 600/437 |
| 6,032,120 A | * | 2/2000 | Rock et al. ..................... | 705/2 |
| 6,076,166 A | * | 6/2000 | Moshfeghi et al. ......... | 713/201 |
| 6,159,150 A | * | 12/2000 | Yale et al. ................... | 600/437 |
| 6,234,969 B1 | * | 5/2001 | Chaintreuil et al. ........ | 600/449 |
| 6,287,257 B1 | * | 9/2001 | Matichuk ..................... | 600/437 |

* cited by examiner

Primary Examiner—Francis J. Jaworski
(74) Attorney, Agent, or Firm—Dorsey & Whitney, LLP

(57) ABSTRACT

An ultrasound imaging system includes a data entry device that reads storage media that is assigned to each patient on which the system is to be used or the operator of the system to obtain ultrasound images. The storage media, which may be a bar code, smartcard, personal digital assistant, for example, contains patient identifying information. The patient or procedure identifying information may be used to access a digital requisition that is referenced by the patient identifying information. The digital requisition may be stored in a disk drive included in the ultrasound imaging system or in a clinical information system accessed through a communication link included in the ultrasound imaging system. The digital requisition may include information pertaining to an ultrasound examination procedure that is to be performed on the patient, which can be used to automatically set up the ultrasound imaging system. The digital requisition may also include the patient's medical history or information about the patient that can be associated with ultrasound images obtained from the patient.

26 Claims, 3 Drawing Sheets

DATA ENTRY AND SETUP SYSTEM AND METHOD FOR ULTRASOUND IMAGING

TECHNICAL FIELD

This invention relates to ultrasound imaging systems, and, more particularly, to a system and method facilitating the entry of examination setup data and other information into an ultrasound imaging system.

BACKGROUND OF THE INVENTION

Ultrasound imaging systems are widely used to obtain a variety of ultrasound images. The imaging systems may be used to scan different parts of the body and the same parts of the body using different techniques or imaging modalities. For example, the arm of a patient may be scanned by placing an ultrasound transducer against different surfaces of the arm to obtain images from different directions. Further, each image may be obtained by either keeping the ultrasound transducer stationery or scanning the transducer across the surface of the skin while the image is being obtained. To obtain the proper image, the operator of the imaging system must be informed of the type of image requested for the patient and the imaging system must be configured in accordance with that information.

Several techniques are conventionally used to set up ultrasound imaging systems. The most basic technique is for the operator of the ultrasound imaging system to simply read the necessary information from a chart for the patient and then set up the imaging system for the examination procedure that is to be performed. The operator also generally enters patient identifying information, such as the patient's name or identification number, so that the identifying information can be displayed on a recording of the image. The procedure description and patient information are generally entered from a menu asking for the entry of specified information.

There are several disadvantages and problems with the above-described technique. First, it requires a substantial period of time for the operator to read the chart, enter patient identifying information and/or other data into the system, and then set up the imaging system for the image requested in the chart. Second, this technique is prone to errors because it is fairly easy for an operator to misread the chart. Even if the chart is read correctly, the operator may incorrectly set up the imaging system for the procedure that is to be performed. The operator may also incorrectly enter the patient identifying information.

Attempts have been made to solve the above-described productivity and error problems. One approach is to interface an ultrasound imaging system with a clinical information system that is maintained by many health-care providers. The clinical information system stores information about the patient, the procedures that are to be performed on the patient, information about physicians responsible for the patient, the patient's medical history, insurance information, and other information pertaining to the patient. The ultrasound imaging system may interface with the clinical information system through various means, such as a local area network or a wireless communication system. In use, the operator obtains patient identifying information from the patient or the patient's chart, and types that information into the ultrasound imaging system. The ultrasound imaging system then transmits the patient identifying information to the clinical information system, which uses the patient identifying information to access information about the patient. The clinical information system then downloads a "digital requisition" to the ultrasound imaging system. The digital requisition includes information specific to the patient, such as the procedures that are to be formed, the name of the patient's physicians, insurance coverage information, medical alerts (HIV status, allergies, etc.) and other information about the patient. The digital requisition may also include information about the patient's medical history, including prior ultrasound images, which can be compared to the image being obtained during the examination procedure.

Although interfacing ultrasound imaging systems to clinical information systems provides significant performance advantages and lessens the possibility of mistakes, it is still less than ideal. It is still possible for the operator to enter the wrong patient identifying information, and thereby receive the wrong digital requisition. Also, it requires significant time for the operator to obtain the correct patient identifying information and enter that information into the imaging system. Finally, it still requires significant time for the operator to properly set up the imaging system, and the operator may set up the imaging system incorrectly or less than optimum for the procedure that is to be performed. Most ultrasound imaging systems are mounted on a wheeled cart. The mobile nature of these ultrasound imaging systems make it difficult to couple them to a central network, which would make it possible to set up the imaging systems from a central location.

Another approach to facilitating the use of medical diagnostic systems is described in U.S. Pat. No. 5,361,755 to Schraag et al. The Schraag et al. system provides an instruction manual for operating a medical monitor. The instruction manual contains clear text instructions for setting up the monitor along with questions for the patient to answer. The instruction manual also includes respective bar codes corresponding to each answer. The patient sets up the monitor in accordance with the instructions, and answers the questions by scanning the bar-code corresponding to the correct answer. The diagnostic information obtained by the monitor, as well as the patient's coded answers, are downloaded to a medical facility for analysis by a healthcare practitioner. The codes may also be decoded by the monitor to provide clear text instructions for operating the monitor. Although the monitor described by Schraag et al. does facilitate the entry of information into the monitor, the entered information does not automatically set up the monitor for any specific purpose nor does it tag the test results with information identifying the patient. As a result, the use of the Schraag et al. monitor is still time-consuming and prone to error.

There is therefore a need for a system that automatically sets up ultrasound imaging systems and automatically enters patient identifying information, thereby minimizing both the use of operator time and the possibility of error in obtaining ultrasound images.

SUMMARY OF THE INVENTION

An ultrasound imaging system in accordance with the invention includes an imaging probe, an ultrasound signal path, a display, a processor, and a data entry device structured to read storage media containing patient identifying information. The ultrasound imager is structured to transmit a query to a mass storage device containing the patient identifying information and to receive a response from a mass storage device containing at least a portion of a digital requisition. The digital requisition stored in the mass storage device contains at least the patient identifying information and information associated with the patient identifying information pertaining to an ultrasound examination procedure that is to be performed on the patient. The processor is structured to transmit a query to the mass storage device containing the patient identifying information and to receive a response from the mass storage device containing at least a portion of the digital requisition. The information contained in the digital requisition may be used to automatically set up the ultrasound imaging system. The information contained in the digital requisition may also be information about the medical history of the patient, or information that is used by the ultrasound imaging system to associate the patient with ultrasound images obtained from the patient using the ultrasound imaging system.

DETAILED DESCRIPTION OF THE INVENTION

Figure 1:
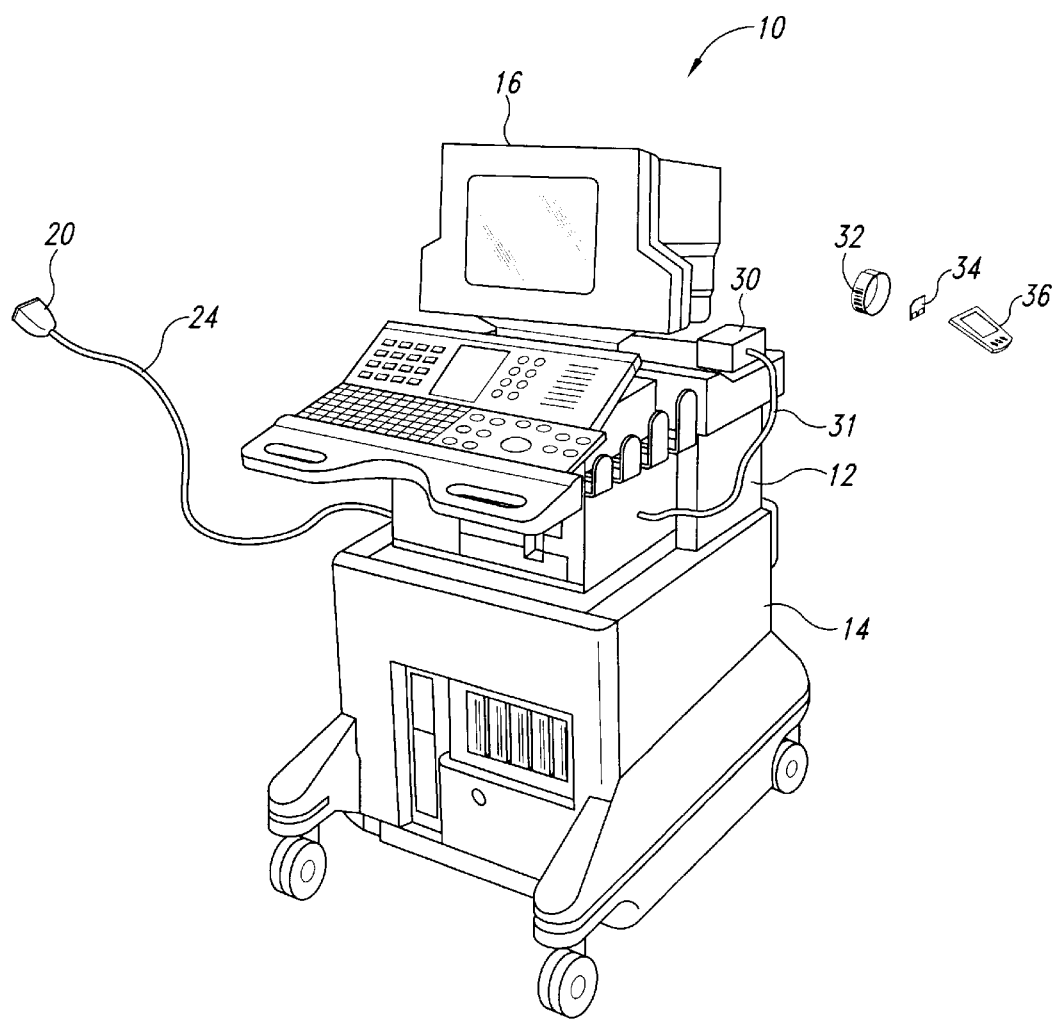
FIG. 1 is an isometric view an ultrasound imaging system in accordance with one embodiment of the present invention.

An ultrasound imaging system 10 in accordance with one embodiment of the invention is illustrated in FIG. 1. The system 10 includes a chassis 12 containing most of the electronic circuitry for the system 10. The chassis 12 is mounted on a cart 14, and a display 16 is mounted on the chassis 12. An ultrasound imaging probe 20 is connected to the chassis 14 by a cable 24. In operation, the probe 20 is placed against the skin of a patient (not shown) and either held stationery or moved to acquire an image of tissues beneath the skin. The image is presented on the display 16, and it may be recorded by a recorder (not shown) or data storage medium (not shown in FIG. 1). Data corresponding to the image may also be downloaded through a suitable data link, such as the Internet or a local area network.

The above-described components of the imaging system 10 are conventional and are commonly used to obtain ultrasound images. The imaging system 10 according to one embodiment of the invention differs from conventional imaging systems by the inclusion of a data entry device 30 coupled to the chassis 12 by a cable 31. In one embodiment, the data entry device 30 comprises a bar-code scanner that is adapted to read bar codes 32 and enter information into the system 10 corresponding thereto. In another embodiment of the invention, the data entry device 30 comprises a "smartcard" reader that is adapted to read information stored in a smartcard 34. In another embodiment of the invention, the data entry device may be a data port to which a personal digital assistant ("PDA") 36 may be coupled. Other devices capable of reading information stored in a variety of media can also be used as the data entry device 30. The data entry device 30 is used in a manner that will be explained in detail in connection with FIG. 3.

Figure 2:
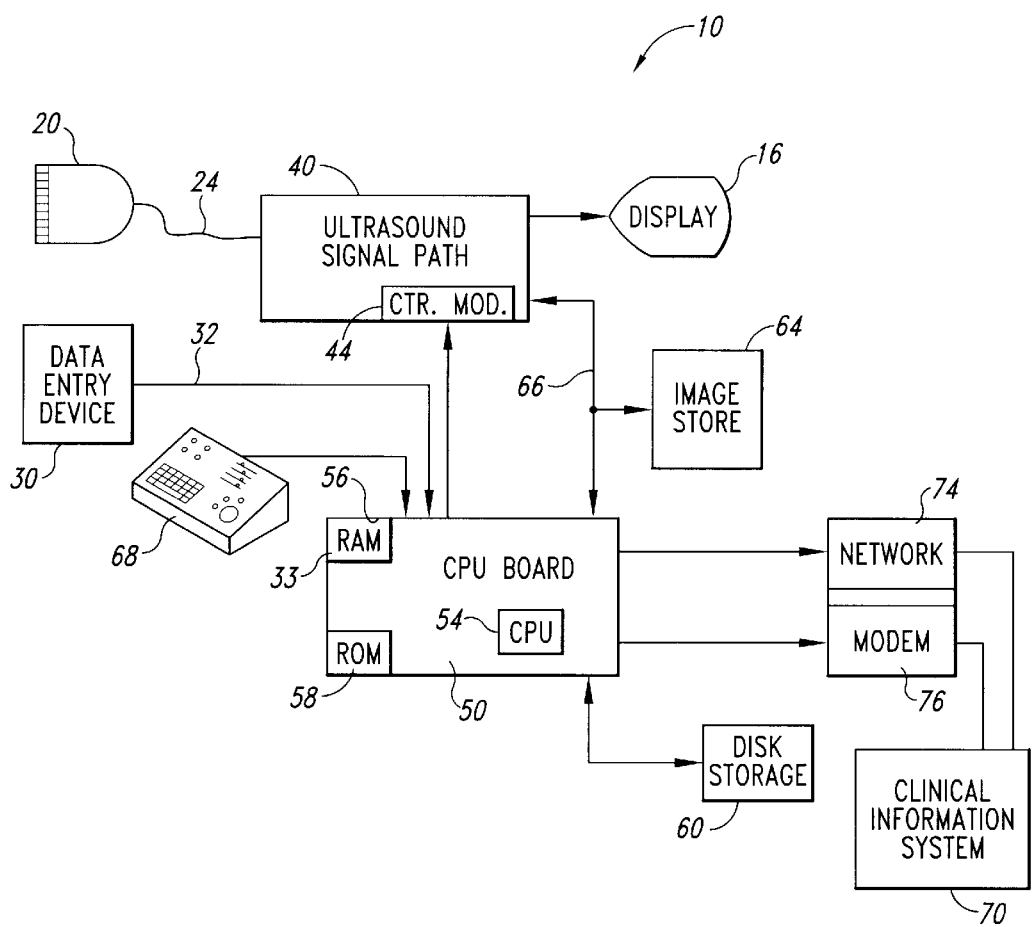
FIG. 2 is a block diagram of pertinent portions of the imaging system of FIG. 1.

The electrical components in the ultrasound imaging system 10 are illustrated in greater detail in FIG. 2. The ultrasound imaging probe 20 is coupled through the cable 24 to an ultrasound signal path 40 of conventional design. As is well-known in the art, the ultrasound signal path 40 includes a transmitter (not shown) coupling electrical signals to the probe 20, an acquisition unit (not specifically shown) that receives electrical signals from the probe 20 corresponding to ultrasound echoes, a signal processing unit (not specifically shown) that processes the signals from the acquisition unit to perform a variety of functions, such as isolating returns from specific depths or isolating returns from blood flowing through vessels, and a scan converter (not specifically shown) that converts the signals from the signal processing unit so that they are suitable for use by the display 16. The ultrasound signal path 40 also includes a control module 44 that controls the operation of the above-described units. The ultrasound signal path 40 may, of course, contain components in addition to those described above, and, it suitable instances, some of the components described above may be omitted.

The control module 44 of the ultrasound signal path 40 interfaces with a central processor unit ("CPU") board 50 containing a number of components, including a CPU 54, random access memory ("RAM") 56, and read only memory ("ROM") 58, to name a few. As is well-known in the art, the ROM 58 stores a program of instructions that are executed by the CPU 54, as well as initialization data for use by the CPU 54. The RAM 56 provides temporary storage of data and instructions for use by the CPU 54. The CPU board 50 interfaces with a mass storage device, such as a disk storage drive 60, for permanent storage of data, such as data corresponding to ultrasound images obtained by the system 10. However, such image data is initially stored in an image storage device 64 that is coupled to a signal path 66 extending between the ultrasound signal path 40 and the CPU board 50.

The CPU board 50 also interfaces with the data entry device 30, as explained above, and a control panel 68, which provides for the manual entry of information. The CPU board 50 may also interface with remote systems, such as a clinical information system 70, by suitable means, such as a local area network 74, a modem 76 or a wireless communication link 78.

Figure 3:
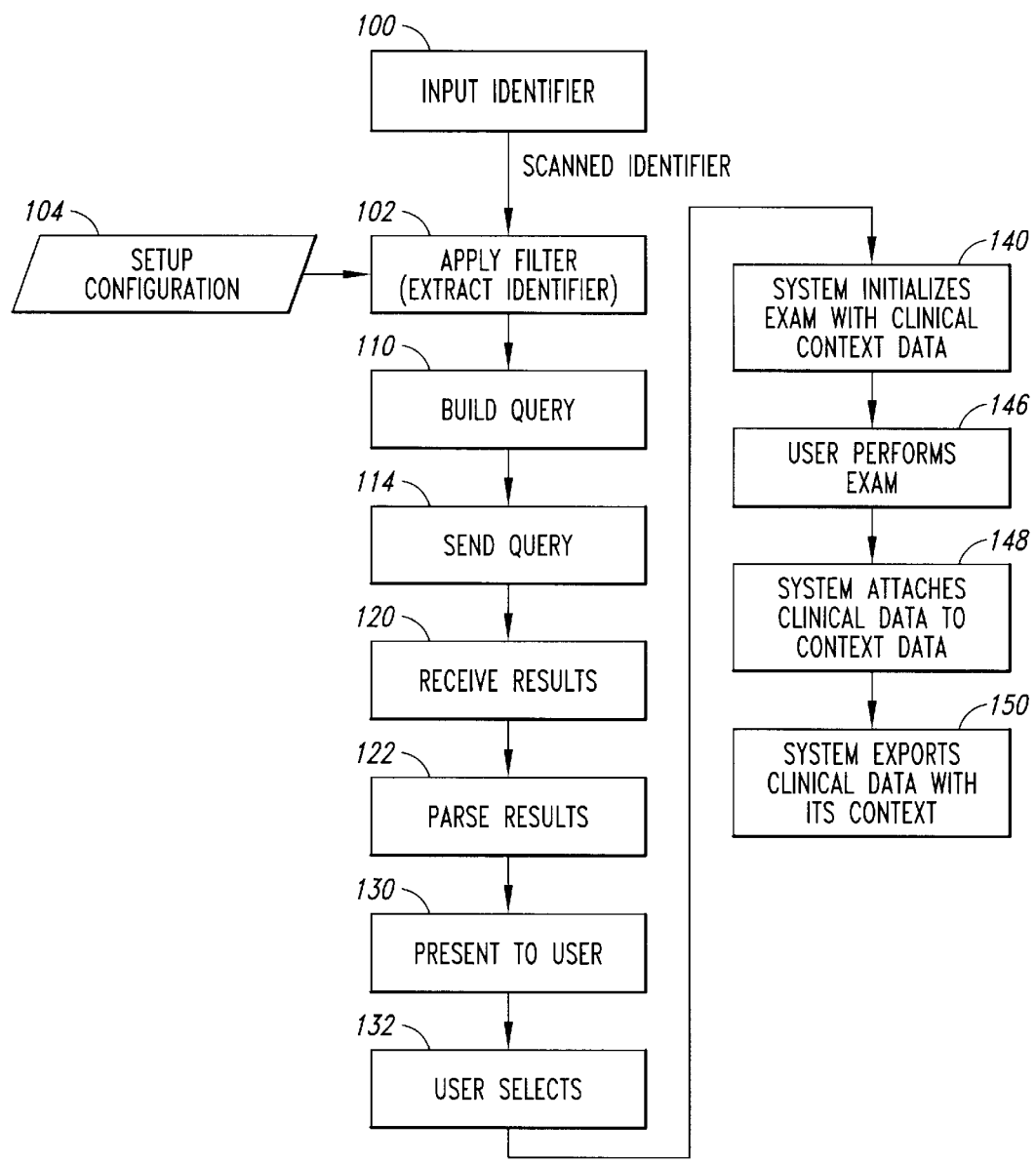
FIG. 3 is a flowchart showing the software executed by a processor in the imaging system of FIG. 1 and showing the method in which the imaging system of FIG. 1 operates.

The operation of the ultrasound imaging system 10 will now be explained with reference to FIG. 3. FIG. 3 comprises a flowchart showing the operation of the ultrasound imaging system 10, which is controlled by the CPU 54 in accordance with a program stored in the ROM 58. The flowchart of FIG. 3 thus also constitutes an explanation of the software stored in the ROM 58 that is executed by the CPU 54.

The operation begins at step 100, where an operator uses the data entry device 30 to enter patient identifying data from storage media. For example, as mentioned above, the patient may wear a wrist band containing the bar-code 32 that can be scanned by a bar-code scanner used as the data entry device 30. The patient may alternatively be provided with the smartcard 34 containing, among other things, patient identifying data that can be read by a smartcard reader used as the data entry device 30. As also stated earlier, the storage media may be a personal digital assistant ("PDA") 36, which interfaces with a data port used as the data entry device 30. Other data storage media may also be read by the data entry device 30. The data storage media, whether it is a bar-code 32, smartcard 34, PDA 36, or some other device, is preferably carried by the patient to avoid incorrect patient identifying data being entered into the ultrasound imaging system 10.

The data read by the data entry device 30 is then filtered at step 102 to extract patient and/or procedure identifying data in the event the data storage media read by the data entry device 30 contains information in addition to patient identifying data. The filtering at step 102 is performed in accordance with examination setup data provided at step 104. The setup data is preferably in the form of a template that identifies the location of the data that should be entered, since the storage media may store data in addition to that data of interest. The template also preferably identifies the significance of the entered data, e.g., whether the entered data is a patient identifier, accession number, etc. The ultrasound imaging system 10 then builds a query at step 110 using the information extracted at step 102. The query preferably specifies the information that is to be returned in response to the query. For example, in addition to providing a patient number, the query may specify that a response should include information identifying the type of images that are to be obtained and the name of the physician responsible for the patient.

The query is then sent to a database containing appropriate information at step 114. The database may be an internal database stored in the disk drive unit 60, or it may be an external database stored in, for example, the clinical information system 70 (FIG. 2). If the database is internal, the data may be provided to the system 10 through a variety of means, such as by periodically downloading the data to the system 10 from the clinical information system 70 or some other source. In either case, the database contains the patient identifying information extracted at step 102 as well as other pertinent information such as the images that should be obtained for such patient.

A response to the query sent at 114 is ultimately received at step 120. The response preferably contains at least the data specified in the query at step 110. The response data is preferably parsed at step 122 to convert the data received in the response to a representation that can be viewed by the operator. The ultrasound imaging system 10 then presents the scheduled exam information to the operator at step 130 using the display 16. For example, the system 10 may display the type of exam to be performed, the type of image to be obtained, the name of the responsible physician, the name of the referring physician, and other clinically relevant information.

The operator of the ultrasound imaging system 10 then views the information on the display 16 presented at step 130 and selects an examination procedure to be performed at step 132, since more than one examination procedure may be scheduled yet only one procedure may be performed at a time. The operator can select an exam at step 132 through a variety of means, such as by "clicking" on a schedule procedure item using a pointing device, using the control panel 68, or other suitable means. The nature of the selection will, of course, depend to some extent upon the manner in which the information is displayed at step 130.

The ultrasound imaging system 10 then reads information corresponding to the selected examination procedure and automatically sets up itself at step 140 in accordance with such information. The system 10 may also copy pertinent data at step 140 so that such data can later be associated with image data generated by the system 10 as a result of the examination procedure. The operator then performs the examination procedure at step 146 in a conventional manner.

The ultrasound imaging system 10 attaches the clinical data, i.e., data received at step 120, with context data, i.e., data corresponding to the image obtained in the exam, at step 148 so that the proper patient data is permanently associated with the image obtained from the patient. Finally, the ultrasound imaging system 10 exports the combined clinical data and context data at step 150, preferably to the clinical information system 70. However, the clinical data could instead or in addition be downloaded to the smartcard 82 or PDA 84 carried by the patient.

It is thus seen that the ultrasound imaging system 10 may be set up by the operator in very little time since it is only necessary to read patient identifying data using the data entry device 30. Thereafter the ultrasound imaging system 10 may be automatically set up and the patient identifying, data may be automatically associated with the image obtained from the patient, thereby minimizing the chances of error.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A configurable ultrasound imaging system, comprising:
portable storage media storing data including patient identifying information identifying a specific patient and information identifying an ultrasound examination procedure that is to be performed on the specific patient, the portable storage media being one of a bar code, smart card and a personal digital assistant; and
an ultrasound imager including an imaging probe, an ultrasound signal path, a display, a processor, a mass storage device storing a digital requisition for the patient, the digital requisition containing at least the patient identifying information and information associated with the ultrasound examination procedure that is to be performed on the specific patient, and a data entry device structured to read the storage media to obtain the patient identifying information and the information identifying the ultrasound examination procedure that is to be performed on the specific patient, the ultrasound imager being structured to transmit a query to the mass storage device containing the patient identifying information and the information associated with the ultrasound examination procedure that is to be performed on the specific patient and to receive a response from the mass storage device containing at least a portion of the digital requisition, the ultrasound imager further being structured to use the digital requisition to set up the ultrasound imager to perform the examination procedure.

2. The system of claim 1 wherein the processor is structured to set up the ultrasound system to perform an ultrasound examination procedure in accordance with the digital requisition received from the mass storage device.

3. The system of claim 1, wherein the processor is structured to set up the ultrasound system to perform an ultrasound examination procedure in accordance with the patient identifying information received from the storage media and the information associated with the ultrasound examination procedure that is to be performed on the specific patient.

4. The system of claim 1, wherein the mass storage device comprises a disk drive included in the ultrasound imager.

5. The system of claim 1 wherein the mass storage device is operable to store ultrasound images obtained using the ultrasound imager, the mass storage device further being operable to store the patient identifying information and the information associated with the ultrasound examination procedure that is to be performed on the specific patient in a manner that associates the patient identifying information and the information associated with the ultrasound examination procedure that is to be performed on the specific patient with the ultrasound images.

6. The system of claim 5, further comprising a communication link included in the ultrasound imager, the communication link being operable to transmit the stored ultrasound images and associated patient identifying information.

7. An ultrasound imaging system, comprising:
  portable storage media storing data including patient identifying information identifying a specific patient and information identifying an ultrasound examination procedure that is to be performed on the specific patient, the portable storage media being one of a bar code, smart card and a personal digital assistant; and
  an ultrasound imager including an imaging probe, an ultrasound signal path, a display, a processor, and a data entry device structured to read the portable storage media to obtain the patient identifying information and the information identifying an ultrasound examination procedure that is to be performed on the specific patient, the ultrasound imager being structured to use the patient identifying information and the information identifying the ultrasound examination procedure that is to be performed on the specific patient to access a digital requisition and to set up the ultrasound system to perform an ultrasound examination procedure in accordance with the digital requisition, the ultrasound imager also being structured to obtain an ultrasound image.

8. The ultrasound imaging system of claim 7, wherein the storage media comprises a bar code, and wherein the data entry device comprises a bar code reader coupled to the processor in the ultrasound imager.

9. The ultrasound imaging system of claim 7, wherein the storage media comprises a smartcard, and wherein the data entry device comprises a smartcard reader coupled to the processor in the ultrasound imager.

10. The ultrasound imaging system of claim 7, wherein the storage media comprises a personal digital assistant, and wherein the data entry device comprises an interface port for the personal digital assistant coupled to the processor in the ultrasound imager.

11. The ultrasound imaging system of claim 7, further comprising a mass storage device storing the digital requisitions for a plurality of patients, each of the digital requisitions containing respective patient identifying information and information pertaining to the patient associated with the respective patient identifying information wherein the ultrasound imager is structured to use the patient identifying information to transmit a query to the mass storage device containing at least a portion of the digital requisition and further wherein the processor is structured to set up the ultrasound system to perform an ultrasound examination procedure in accordance with the digital requisition received from the storage media.

12. The ultrasound imaging system of claim 11 wherein the mass storage device is operable to store ultrasound images obtained using the ultrasound imager, the mass storage device further being operable to store the patient identifying information in a manner that associates the patient identifying information with the ultrasound images.

13. The ultrasound imaging system of claim 12 wherein the ultrasound imager is further operable to associate information obtained from the digital requisition with the obtained ultrasound image.

14. The ultrasound imaging system of claim 13 wherein the ultrasound imager is further operable to download the ultrasound image and associated information obtained from the digital requisition to the mass storage device.

15. An ultrasound imaging system, comprising:
  an ultrasound imaging probe;
  an ultrasound signal path;
  a display;
  a mass storage device;
  a data entry device structured to read portable storage media containing patient identifying information identifying a specific patient and information identifying an ultrasound examination procedure that is to be performed on the specific patient, the data entry device being one of a bar code reader, smart card reader and a personal digital assistant interface; and
  a processor coupled to the ultrasound signal path, the display, the data entry device, and the mass storage device, the processor being operable to obtain from the data entry device the patient identifying information and the information identifying the ultrasound examination procedure that is to be performed on the specific patient, obtain procedure information identifying an examination procedure associated with the patient identifying information and the information identifying the ultrasound examination procedure that is to be performed on the specific patient, and to automatically set up the ultrasound system to perform the ultrasound examination procedure in accordance with the obtained procedure information.

16. The ultrasound imaging system of claim 15, wherein the mass storage device comprises a disk drive.

17. A method of configuring an ultrasound imaging system, comprising:
  providing portable storage media storing data including patient identifying information identifying a specific patient and information identifying an ultrasound examination procedure that is to be performed on the specific patient, the portable storage media being one of a bar code, a smart card and a personal digital assistant;
  using the ultrasound imaging system to read the storage media to obtain the patient identifying information and the information identifying the ultrasound examination procedure that is to be performed on the specific patient;
  using the patient identifying information and the information identifying the ultrasound examination procedure that is to be performed on the specific patient access a digital requisition containing information about one of the patient and the examination procedure; and
  using the digital requisition to automatically set up the ultrasound system to perform the ultrasound examination procedure.

18. The method of claim 17, wherein the act of using the patient identifying information to automatically set up the ultrasound system to perform the ultrasound examination procedure comprises:
  using the patient identifying information to access a digital requisition for the patient from internal mass storage media, the digital requisition containing at least the patient identifying information and information associated with the patient identifying information pertaining to an ultrasound examination procedure that is to be performed on the patient;
  obtaining from the accessed digital requisition information pertaining to the ultrasound examination procedure that is to be performed; and
  using the information pertaining to the ultrasound examination procedure that is to be performed to automatically set up the ultrasound system to perform the ultrasound examination procedure.

19. The method of claim 18, wherein the act of using the patient identifying information to automatically set up the ultrasound system to perform the ultrasound examination procedure comprises:

providing the ultrasound imaging system with mass storage media; and periodically storing digital requisitions for a plurality of patients in the mass storage media.

20. The method of claim 18, further comprising obtaining ultrasound images using the ultrasound imaging system;

obtaining from the accessed digital requisition information pertaining to the patient; and associating the obtained information pertaining to the patient with the obtained ultrasound images.

21. The method of claim 20 further comprising uploading the obtained ultrasound images and associated information pertaining to the patient to the mass storage media.

22. The method of claim 18, wherein the digital requisition includes information about the medical history of the patient, and wherein the method further includes obtaining from the accessed digital requisition the information about the medical history of the patient and displaying information about the medical history of the patient.

23. A method of using an ultrasound imaging system to obtain ultrasound images and associate the images with a patient from which the ultrasound images were obtained, the method comprising:

providing portable storage media storing data including patient identifying information identifying a specific patient and information identifying an ultrasound examination procedure that is to be performed on the specific patient, the portable storage media being one of a bar code, smart card and a personal digital assistant;

using the ultrasound imaging system, to obtain at least one of ultrasound images, worksheet data, measurements, and calculations from the patient;

using the ultrasound imaging systems to read the portable storage media to obtain the patient identifying information and the information identifying the ultrasound examination procedure that is to be performed on the specific patient, and automatically associating with the images obtained from the patient the patient identifying information and the information identifying the ultrasound examination procedure that is to be performed on the specific patient.

24. The method of claim 23, wherein the act of automatically associating with the images obtained from the patient the patient identifying information and the information identifying the ultrasound examination procedure that is to be performed on the specific patient comprise:

using the patient identifying information and the information identifying the ultrasound examination procedure that is to be performed on the specific patient to access a digital requisition for the patient, the digital requisition containing information about the patient that is to be associated with the images obtained from the patient; and obtaining from the accessed digital requisition the information about the patient that is to be associated with the images.

25. The method of claim 23, wherein the act of automatically associating with the images obtained from the patient the patient identifying information and the information associated with the ultrasound examination procedure that is to be performed on the specific patient comprise:

providing the ultrasound imaging system with mass storage media;

periodically storing information about a plurality of patients in the mass storage media, the stored information being associated with respective patient identifying information and the information associated with the ultrasound examination procedure that is to be performed on the specific patient;

using the patient identifying information and the information associated with the ultrasound examination procedure that is to be performed on, the specific patient read from the portable storage media to access the information about the patient corresponding to the read patient identifying information and the information associated with the ultrasound examination procedure that is to be performed on the specific patient; and obtaining the information about the patient from the mass storage media.

26. The method of claim 23, further comprising uploading the obtained ultrasound images and associated patient identifying information to the mass storage media.

* * * * *